(12) United States Patent
Rao et al.

(10) Patent No.: US 9,999,606 B2
(45) Date of Patent: *Jun. 19, 2018

(54) ORAL PHARMACEUTICAL COMPOSITION OF ISOTRETINOIN

(71) Applicant: Sun Pharmaceutical Industries Limited, Mumbai, Maharashtra (IN)

(72) Inventors: Rajesh Rao, Uttar Pradesh (IN); Anuj Kumar Fanda, Uttar Pradesh (IN); Satish Kumar Jain, Chhattisgarh (IN); Romi Barat Singh, Uttar Pradesh (IN)

(73) Assignee: Sun Pharmaceutical Industries Limited., Mumbai (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/958,238

(22) Filed: Dec. 3, 2015

(65) Prior Publication Data

US 2016/0089353 A1 Mar. 31, 2016

Related U.S. Application Data

(63) Continuation of application No. PCT/IB2015/054087, filed on May 29, 2015.

(30) Foreign Application Priority Data

| May 29, 2014 | (IN) | ............................. 1422/DEL/2014 |
| Jun. 30, 2014 | (IN) | ............................. 1736/DEL/2014 |
| Dec. 1, 2014 | (IN) | ............................. 3488/DEL/2014 |

(51) Int. Cl.
| *A61K 31/203* | (2006.01) |
| *A61K 9/48* | (2006.01) |
| *A61K 9/14* | (2006.01) |

(52) U.S. Cl.
CPC ............ *A61K 31/203* (2013.01); *A61K 9/143* (2013.01); *A61K 9/145* (2013.01); *A61K 9/146* (2013.01); *A61K 9/4833* (2013.01); *A61K 9/485* (2013.01); *A61K 9/4858* (2013.01); *A61K 9/4866* (2013.01)

(58) Field of Classification Search
CPC ........ A61K 9/143; A61K 9/145; A61K 9/146; A61K 9/4833; A61K 9/485; A61K 9/4858; A61K 9/4866; A61K 31/203
See application file for complete search history.

(56) References Cited

U.S. PATENT DOCUMENTS

| 7,435,427 | B2 | 10/2008 | Vanderbist et al. | ........... 424/439 |
| 8,367,102 | B2 | 2/2013 | Vanderbist et al. | ........... 424/451 |
| 2003/0180352 | A1* | 9/2003 | Patel | ................... A61K 9/1617 |
| | | | | 424/465 |
| 2005/0129773 | A1* | 6/2005 | Bhatia | ...................... A61K 9/14 |
| | | | | 424/489 |
| 2008/0044486 | A1 | 2/2008 | Nilsson et al. | |
| 2014/0107203 | A1* | 4/2014 | Deboeck | .............. A61K 9/4875 |
| | | | | 514/559 |
| 2015/0150822 | A1* | 6/2015 | Perumal | ................. A61K 47/42 |
| | | | | 424/499 |

FOREIGN PATENT DOCUMENTS

| WO | WO 00/25772 | 5/2000 | .......... A61K 31/203 |
| WO | WO 2005/023228 | 3/2005 | .............. A61K 9/24 |
| WO | WO 2005023228 A1 * | 3/2005 | .......... A61K 9/0004 |
| WO | WO 2010/134047 | 11/2010 | .............. A61P 17/10 |
| WO | WO 2012/053013 | 4/2012 | ............. A61K 9/107 |

OTHER PUBLICATIONS

Cipher Pharmaceuticals Inc., EPURIS product monograph, Mar. 14, 2013, pp. 1-38.*
Veena et al., "Pelletization Technique in Drug Delivery System—A Review," *International Journal of Pharmaceutical Development & Technology*, 3(1):13-22 (2013).
Cipher Pharmaceuticals Inc., Epuris product monograph. Mar. 14, 2013 (retrieved on Aug. 29, 2015). Retrieved from: http://www.cipherpharma.com/download/epuris_july2015.pdf.
EPO Extended Search Report dated Nov. 21, 2017 for EPO Patent Application No. 15800660.1.

* cited by examiner

*Primary Examiner* — Michael B. Pallay
(74) *Attorney, Agent, or Firm* — Liang, Frank & King, LLP; Stanley D. Liang

(57) ABSTRACT

An oral pharmaceutical composition of isotretinoin and a carrier substrate, having isotretinoin in the form of gel, dispersion, solution or emulsion, which is absorbed onto the carrier substrate to form solid particles, powder, or granules. The oral pharmaceutical composition has enhanced bioavailability. A process is used for preparing the oral composition.

24 Claims, No Drawings

ORAL PHARMACEUTICAL COMPOSITION OF ISOTRETINOIN

FIELD OF THE INVENTION

The present invention provides an oral pharmaceutical composition of isotretinoin having enhanced bioavailability. The present invention further relates to a process for preparing the oral pharmaceutical composition of the present invention.

BACKGROUND OF THE INVENTION

Isotretinoin is a retinoid (also known as 13-cis retinoic acid). Owing to its low water solubility, the oral bioavailability of isotretinoin is low. PCT Publication No. WO 00/25772 discloses that the presently marketed formulation of isotretinoin, i.e., Accutane®, contains isotretinoin at a mean particle size of about 100 µm resulting in only 20% oral bioavailability. Therefore, this application discloses a formulation of isotretinoin having a reduced particle size, thereby enhancing the oral bioavailability.

U.S. Pat. Nos. 7,435,427 and 8,367,102 cover the marketed formulation of Absorica®. These patents disclose capsules comprising a semi-solid suspension of isotretinoin containing at least two lipidic excipients, one having an HLB value equal to or greater than 10 and the other being an oily vehicle. These patents are based on the use of the "Lidose technology" to provide a formulation of isotretinoin with enhanced bioavailability.

The oral bioavailability of a drug is affected by various factors which include the aqueous solubility, first pass effect, or food-effect. The low water solubility of isotretinoin affects its oral bioavailability. Therefore, there is a need to develop an oral pharmaceutical composition of isotretinoin having enhanced bioavailability. The present inventors have developed an oral pharmaceutical composition of isotretinoin having enhanced bioavailability in comparison to the already marketed formulations of isotretinoin, i.e., Roaccutane® and Absorica®/Epuris™. This enhancement in bioavailability of isotretinoin by the present invention can be directly correlated to dose reduction of isotretinoin, which would be highly beneficial in the case of isotretinoin, which is a teratogenic drug.

SUMMARY OF THE INVENTION

The present invention provides an oral pharmaceutical composition of isotretinoin having enhanced bioavailability. This enhancement in the bioavailability in comparison to the already marketed formulations of isotretinoin, i.e., Roaccutane® and Absorica®/Epuris™, can be directly correlated with the reduction in dose in order to have a bioequivalent product. The oral pharmaceutical composition of the present invention comprises isotretinoin and a pharmaceutically acceptable excipient and is in the form of solid particles, powder, or granules. Solid particles, powder, or granules may further be filled into capsules or processed with tablet adjuvants and compressed into tablets. The present invention further provides a process for preparing the oral pharmaceutical composition of the present invention. It also provides a method of treating acne by administering the oral pharmaceutical composition of the present invention.

DETAILED DESCRIPTION OF THE INVENTION

In one aspect, the present invention provides an oral pharmaceutical composition of isotretinoin having enhanced bioavailability wherein said composition exhibits improved pharmacokinetic profile as compared to Epuris™ capsules under fed as well as fasting conditions at the same dosage levels.

In one embodiment of the above aspect, said composition exhibits a mean $C_{max}$ and AUC under fed condition which is about 1.25 and about 1.16 times higher than the mean $C_{max}$ and AUC of Epuris™ capsules under fed condition, respectively.

In another embodiment of the above aspect, said composition exhibits a mean $C_{max}$ and AUC under fasting condition which is about 3.4 and about 2.5 times higher than the mean $C_{max}$ and AUC of Epuris™ capsules under fasting condition, respectively.

In another embodiment of the above aspect, said composition releases more than 50% of isotretinoin in 15 minutes in a media with a pH of 7.4 to 10.5.

In another embodiment of the above aspect, said enhancement in the bioavailability is directly correlated to the reduction in dose in order to have a bioequivalent product.

In another embodiment of the above aspect, said dose is reduced by at least 10% in comparison to the marketed Epuris™ capsules.

In another embodiment of the above aspect, said dose is reduced by at least 20% in comparison to the marketed Epuris™ capsules.

In another aspect, the present invention provides an oral pharmaceutical composition of isotretinoin having enhanced bioavailability, wherein said composition comprises isotretinoin and a pharmaceutically acceptable excipient.

In another aspect, the present invention provides an oral pharmaceutical composition of isotretinoin having enhanced bioavailability wherein isotretinoin is dissolved or dispersed in a liquid vehicle selected from water, a water-miscible solvent, or a combination thereof.

In another aspect, the present invention provides an oral pharmaceutical composition of isotretinoin having enhanced bioavailability wherein said composition comprises isotretinoin and a carrier substrate.

In another embodiment of the above aspect, the carrier substrate is present in an amount of about 1% w/w to about 90% w/w by total weight of the composition, preferably in an amount of about 1% w/w to about 70% w/w by total weight of the composition.

In another embodiment of the above aspect, the carrier substrate is present in an amount of about 20% w/w to about 85% w/w by total weight of the composition.

In another embodiment of the above aspect, said composition further comprises a surfactant, a surface-stabilizer, an antioxidant, or an alkaline stabilizer.

In another embodiment of the above aspect, said composition comprises isotretinoin, meglumine, a surface stabilizer, a surfactant, and a carrier substrate.

In one embodiment of the above aspect, said composition is in the form of a gel, a dispersion, a solution, a suspension, or an emulsion.

In yet another embodiment of the above aspect, said gel, dispersion, solution, suspension, or emulsion is filled into capsules.

In yet another embodiment of the above aspect, said gel, dispersion, solution, suspension, or emulsion is absorbed or loaded onto a carrier substrate to form solid particles, powder, or granules.

In another embodiment of the above aspect, the solid particles, powder, or granules are filled into capsules.

In still another embodiment of the above aspect, the solid particles, powder, or granules are processed with tablet adjuvants and compressed into tablets.

In another embodiment of the above aspect, said composition comprises isotretinoin in an amount of about 1 mg to 100 mg, 5 mg to 50 mg, 10 mg to 40 mg, 9 mg to 36 mg, or 8 mg to 32 mg.

In another embodiment of the above aspect, said composition comprises isotretinoin in an amount of about 40 mg.

In another embodiment of the above aspect, said composition comprises isotretinoin in an amount of about 32 mg.

In another embodiment of the above aspect, said composition comprises isotretinoin in an amount of about 16 mg.

In yet another embodiment of the above aspect, the composition comprises isotretinoin wherein the particle size distribution of isotretinoin is such that $D_{90}$ is less than 60 µm, less than 55 µm, less than 50 µm, less than 45 µm, less than 40 µm, less than 35 µm, less than 30 µm, less than 25 µm, less than 20 µm, less than 15 µm, or less than 10 µm.

In yet another embodiment of the above aspect, the composition comprises isotretinoin wherein the particle size distribution of isotretinoin is such that $D_{90}$ is less than 10 µm.

In another embodiment of the above aspect, the composition comprises isotretinoin wherein the particle size distribution of isotretinoin is such that $D_{50}$ is less than 40 µm, less than 35 µm, less than 30 µm, less than 25 µm, less than 20 µm, less than 15 µm, less than 10 µm, or less than 5 µm.

In yet another embodiment of the above aspect, the composition comprises isotretinoin wherein the particle size distribution of isotretinoin is such that $D_{50}$ is less than 5 µm.

In another embodiment of the above aspect, the composition comprises isotretinoin wherein the particle size distribution of isotretinoin is such that $D_{10}$ is less than 20 µm, less than 18 µm, less than 17 µm, less than 15 µm, less than 12 µm, less than 10 µm, less than 8 µm, less than 7 µm, less than 5 µm, or less than 2 µm.

In yet another embodiment of the above aspect, the composition comprises isotretinoin wherein the particle size distribution of isotretinoin is such that $D_{10}$ is less than 2 µm.

In yet another embodiment of the above aspect, the composition comprises isotretinoin wherein the particle size distribution of isotretinoin is such that $D_{90}$ is less than 60 µm and $D_{50}$ is less than 40 µm.

In yet another embodiment of the above aspect, the composition comprises isotretinoin wherein the particle size distribution of isotretinoin is such that $D_{90}$ is less than 60 µm, $D_{50}$ is less than 40 µm, and $D_{10}$ is less than 20 µm.

In yet another embodiment, the composition is stable when stored at 40° C. and 75% relative humidity or at 25° C. and 60% relative humidity for a period of at least three months or to the extent necessary for the use of the composition.

In another aspect, the present invention provides a process for preparing an oral pharmaceutical composition of isotretinoin having enhanced bioavailability wherein said process comprises wet or dry granulation, using fluidized bed granulator or high shear mixer granulator, direct compression, extrusion-spheronization, melt granulation/extrusion, spray-drying, spray-congealing, freeze-drying, or any other conventional process known in the art.

In one embodiment of the above aspect, said process comprises the following steps:
(a) dissolving/dispersing an antioxidant in water, a water-miscible solvent, or a combination thereof;
(b) adding one or more excipients selected from a surfactant, a surface-stabilizer, and an alkaline stabilizer to the solution or dispersion of step (a) to form a gel, a dispersion, a solution, a suspension, or an emulsion;
(c) dissolving/dispersing isotretinoin into the gel, dispersion, solution, suspension, or emulsion of step (b);
(d) optionally milling the gel, dispersion, solution, suspension, or emulsion of step (c);
(e) adsorbing/loading the gel, dispersion, solution, suspension, or emulsion of step (d) onto a carrier substrate to obtain solid particles, powder, or granules; and filling the solid particles, powder, or granules of step (e) into capsules or processing the solid particles, powder, or granules of step (e) with tablet adjuvants and compressing into tablets.

In another aspect, the present invention provides a process for preparing an oral pharmaceutical composition of isotretinoin having enhanced bioavailability comprising:
(a) isotretinoin;
(b) meglumine;
(c) a surfactant;
(d) a surface stabilizer; and
(e) a carrier substrate
wherein the process comprises:
i. dissolving/dispersing meglumine, a surfactant and a surface stabilizer in water;
ii. dispersing isotretinoin into the solution of step i;
iii. milling the dispersion of step ii in a milling apparatus;
iv. adsorbing the milled dispersion of step iii onto a carrier substrate to obtain solid particles, powder, or granules; and
v. filling the solid particles, powder, or granules of step iv into capsules or processing the solid particles, powder, or granules of step iv with tablet adjuvants and compressing into tablets.

In an embodiment of the above aspect, an antioxidant may be added along with meglumine.

In another embodiment of the above aspect, the pH of the dispersion obtained in step iii or the solid particles or powder or granules obtained in step iv when dispersed in water ranges from 3 to 11; preferably the pH ranges from 7 to 10.

In still another aspect, the present invention provides a method of treating acne, musculoskeletal and connective tissue inflammations, emphysema, ulcerating diseases, cervical tumors in HIV positive women, lung cancer in smokers, skin cancer, neuroblastoma, recurrent prostate cancer, leukemia, high-grade glioma, head and neck cancers, multiple myeloma, gram-negative folliculitis, recalcitrant rosacea, pyoderma faciale, psoriasis, cutaneous lupus erythematosus, acne fulminans, squamous cell carcinoma, or cutaneous photoaging by administering to the individual in need thereof the oral pharmaceutical composition of the present invention.

In one embodiment of the above aspect, the present invention provides a method of treating acne by administering to the individual in need thereof the oral pharmaceutical composition of the present invention.

The term "isotretinoin" refers to isotretinoin in its crystalline or amorphous form, its esters, salts, or derivatives thereof.

The term "AUC" refers to the area under the time/plasma concentration curve after administration of the pharmaceutical composition. $AUC_{0\text{-}Infinity}$ denotes the area under the plasma concentration versus time curve from time 0 to infinity; $AUC_{0\text{-}t}$ denotes the area under the plasma concentration versus time curve from time 0 to time t.

The term "$C_{max}$" refers to the maximum concentration of isotretinoin in the blood following administration of the pharmaceutical composition.

The term "$t_{max}$" refers to the time in hours when $C_{max}$ is achieved following administration of the pharmaceutical composition.

The term "food effect" as used herein means food-drug interactions which either decrease or increase the extent of drug absorption. It refers to a relative difference in AUC, $C_{max}$, and/or $t_{max}$ of a drug, when said drug or a formulation thereof is administered orally to a human, concomitantly with food or in a fed state as compared to the same values when the same formulation is administered in a fasted state or without food.

The term "$D_{10}$" refers to the particle size of isotretinoin where 10% (w/v) of the particles have a size less than the defined $D_{10}$ value; "$D_{50}$" refers to the particle size of isotretinoin where 50% (w/v) of the particles have a size less than the defined $D_{50}$ value; "$D_{90}$" refers to the particle size of isotretinoin where 90% (w/v) of the particles have a size less than the defined $D_{90}$ value.

"Defined $D_{10}$ value/$D_{50}$ value/$D_{90}$ value" refers to the values defined in the embodiments.

Examples of suitable liquid vehicles include, but are not limited to, water, propylene glycol, dipropylene glycol, polypropylene glycol, ethylene glycol, polyethylene glycol, glycerin, butylene glycol, hexylene glycol, polyoxyethylene, and mixtures thereof.

Examples of suitable carrier substrates include, but are not limited to, lactose; microcrystalline cellulose; calcium phosphate; dextrin; dextrose; sucrose; mannitol; maltodextrin; sodium alumino silicate; clays, including bentonite, kaolin, montmorrillonite, attapulgite, halloysite, laponite, and the like; silica, including colloidal silica, mesoporous silica, and fumed silica; zeolites; talc; cholesteramine; polystyrene sulfonates; mono and polysulfonated resins; activated charcoal; and mixtures thereof.

Examples of suitable surfactants include, but are not limited to, lecithin; sorbitan monostearate; polysorbates prepared from lauric, palmitic, stearic, and oleic acid; polyoxyethylene monoesters such as polyoxyethyl ethylene monostearate, polyoxyethylene monolaurate, and polyoxyethylene monooleate; dioctyl sodium sulfosuccinate; sodium lauryl sulfate; and poloxamers.

Examples of suitable surface stabilizers include, but are not limited to, gelatin, casein, gum acacia, stearic acid, calcium stearate, glycerol monostearate, sorbitan esters, macrogol ethers such as cetomacrogol 1000, polyoxyethylene castor oil derivatives, polyoxyethylene sorbitan fatty acid esters such as Tween®; polyoxyethylene stearates, colloidal silicon dioxide, sodium dodecyl sulfate, carboxymethylcellulose calcium, carboxymethylcellulose sodium, hydroxyethylcellulose, hydroxypropylcellulose, hydroxypropyl methylcellulose, polyvinylpyrrolidone (PVP), poloxamers such as Pluronics® F 68 and F 108, dioctyl sodium sulfosuccinate (DOSS), docusate sodium, sodium lauryl sulfate, Span® 20 and 80, and macrogolglycerol esters such as Cremophor® EL.

Examples of suitable antioxidants include, but are not limited to, butylated hydroxyl anisole, butylated hydroxyl toluene, tocopherol, ascorbyl palmitate, ascorbic acid, sodium metabisulfite, sodium sulfite, sodium thiosulfate, propyl gallate, and mixtures thereof.

Examples of suitable alkaline stabilizers include, but are not limited to, sodium hydroxide, potassium hydroxide, sodium carbonate or bicarbonate, potassium carbonate or bicarbonate, lithium hydroxide, triethylamine, meglumine, methylamine, and mixtures thereof.

Examples of suitable preservatives include, but are not limited to, methyl paraben, ethyl paraben, propyl paraben, butyl paraben, benzoic acid, sodium benzoate, benzyl alcohol, sorbic acid, potassium sorbate, and mixtures thereof.

Examples of suitable tablet adjuvants include diluents, binders, disintegrants, lubricants, glidants, and mixtures thereof.

The term "stable," as used herein, refers to chemical stability, wherein not more than 1.5% w/w of total related substances are formed on storage at accelerated conditions of stability at 40° C. and 75% relative humidity or at 25° C. and 60% relative humidity for a period of at least three months or to the extent necessary for use of the composition.

The size reduction of isotretinoin is achieved by wet milling the dispersion of isotretinoin in an oily vehicle or the dispersion of isotretinoin in an aqueous medium using mechanical means such as a jet mill, ball mill, and media mills such as a sand mill, DYNO®-mill, or a bead mill. The grinding media in these mills can comprise spherical particles such as stainless steel beads or zirconium oxide balls.

The invention may be further illustrated by the following examples, which are for illustrative purposes only and should not be construed as limiting the scope of the invention in anyway.

EXAMPLES

Example 1

| S. No. | Ingredients | Quantity (% w/w) |
| --- | --- | --- |
| 1 | Isotretinoin | 9.64 |
| 2 | Hydroxypropylmethyl cellulose | 4.82 |
| 3 | Sodium hydroxide | 1.45 |
| 4 | Water | 59.75 |
| 5 | Sodium alumino silicate | 24.10 |
| 6 | Butylated hydroxy anisole | 0.24 |

Procedure

1. Sodium hydroxide was dissolved in water.
2. Hydroxypropylmethyl cellulose was dissolved in the solution of step 1.
3. Butylated hydroxy anisole was dissolved in the solution of step 2.
4. Isotretinoin was dissolved in the solution of step 3 to form a gel.
5. The gel of step 4 was adsorbed onto sodium alumino silicate to form solid particles.
6. The solid particles of step 5 were filled into capsules.

Example 2

| S. No. | Ingredients | Quantity (% w/w) |
| --- | --- | --- |
| 1 | Isotretinoin | 9.64 |
| 2 | Hydroxypropylmethyl cellulose | 4.82 |
| 3 | Sodium hydroxide | 1.45 |
| 4 | Propylene glycol | 59.75 |
| 5 | Sodium alumino silicate | 24.10 |
| 6 | Butylated hydroxy anisole | 0.24 |

Procedure

1. Sodium hydroxide was dissolved in propylene glycol.
2. Hydroxypropylmethyl cellulose was dissolved in the solution of step 1.
3. Butylated hydroxy anisole was dissolved in the solution of step 2.

4. Isotretinoin was dispersed into the solution of step 3 to form a dispersion.

5. The dispersion of step 4 was adsorbed onto sodium alumino silicate to form solid particles.

6. The solid particles of step 5 were filled into capsules.

Example 3

| S. No. | Ingredients | Quantity (% w/w) |
|---|---|---|
| 1 | Isotretinoin | 9.64 |
| 2 | Hydroxypropylmethyl cellulose | 4.82 |
| 3 | Sodium hydroxide | 1.45 |
| 4 | Polyethylene glycol | 59.75 |
| 5 | Sodium alumino silicate | 24.10 |
| 6 | Butylated hydroxy anisole | 0.24 |

Procedure

1. Sodium hydroxide was dissolved in polyethylene glycol.
2. Hydroxypropylmethyl cellulose was dissolved in the solution of step 1.
3. Butylated hydroxy anisole was dissolved in the solution of step 2.
4. Isotretinoin was dispersed into the solution of step 3 to form a dispersion.
5. The dispersion of step 4 was adsorbed onto sodium alumino silicate to form solid particles.
6. The solid particles of step 5 were filled into capsules.

Example 4

| S. No. | Ingredients | Quantity (% w/w) |
|---|---|---|
| 1 | Isotretinoin | 9.64 |
| 2 | Hydroxypropylmethyl cellulose | 4.82 |
| 3 | Sodium hydroxide | 1.45 |
| 4 | Glycerin | 59.75 |
| 5 | Sodium alumino silicate | 24.10 |
| 6 | Butylated hydroxy anisole | 0.24 |

Procedure

1. Sodium hydroxide was dissolved in glycerin.
2. Hydroxypropylmethyl cellulose was dissolved in the solution of step 1.
3. Butylated hydroxy anisole was dissolved in the solution of step 2.
4. Isotretinoin was dispersed into the solution of step 3 to form a dispersion.
5. The dispersion of step 4 was adsorbed onto sodium alumino silicate to form solid particles.
6. The solid particles of step 5 were filled into capsules.

Example 5

| S. No. | Ingredients | Quantity (% w/w) |
|---|---|---|
| 1 | Isotretinoin | 9.64 |
| 2 | Hydroxypropylmethyl cellulose | 4.82 |
| 3 | Sodium hydroxide | 1.45 |
| 4 | Water | 11.56 |
| 5 | Glycerin | 48.19 |
| 6 | Sodium alumino silicate | 24.10 |
| 7 | Butylated hydroxy anisole | 0.24 |

Procedure

1. Sodium hydroxide was dissolved in a mixture of water and glycerin.
2. Hydroxypropylmethyl cellulose was dissolved in the solution of step 1.
3. Butylated hydroxy anisole was dissolved in the solution of step 2.
4. Isotretinoin was dispersed into the solution of step 3 to form a gel.
5. The gel of step 4 was adsorbed onto sodium alumino silicate to form solid particles.
6. The solid particles of step 5 were filled into capsules.

Example 6

| S. No. | Ingredients | Quantity (% w/w) |
|---|---|---|
| 1 | Isotretinoin | 9.97 |
| 2 | Hydroxypropylmethyl cellulose | 5.01 |
| 3 | Sodium hydroxide | 1.50 |
| 4 | Butylated hydroxy anisole | 0.12 |
| 5 | Water | q.s. |
| 6 | Lactose | 78.39 |
| 7 | Cremophor ® EL | 5.01 |

Procedure

1. Sodium hydroxide was dissolved in water.
2. Hydroxypropylmethyl cellulose was dissolved in the solution of step 1.
3. Butylated hydroxy anisole was dissolved in solution of step 2.
4. Isotretinoin was dissolved in the solution of step 3.
5. Cremophor® EL was added to the solution of step 4.
6. The solution of step 5 was adsorbed onto lactose to form solid particles.
7. The solid particles of step 6 were filled into capsules.

Example 7

| S. No. | Ingredients | Quantity (% w/w) |
|---|---|---|
| 1 | Isotretinoin | 20.15 |
| 2 | Meglumine | 4.03 |
| 3 | Water | q.s. |
| 4 | Hydroxypropyl methylcellulose | 5.04 |
| 5 | Lactose | 25.19 |
| 6 | Cremophor ® EL | 45.34 |
| 7 | Butylated hydroxyl anisole | 0.25 |

Procedure

1. Hydroxypropyl methylcellulose was dissolved in water.
2. Butylated hydroxyl anisole and meglumine were dissolved in the solution of step 1.
3. Isotretinoin was suspended in the solution of step 2.
4. The drug suspension of step 3 was milled in a Dyno®-Mill containing zirconium beads to achieve a particle size of isotretinoin such that $D_{90}$ was about 2 μm.
5. Cremophor® EL was added at the end of the milling process.
6. The dispersion of step 5 was adsorbed onto lactose in a fluid bed processor and dried.

7. The dried powder of step 6 was filled into size 00 capsules.

Example 8

| S. No. | Ingredients | Quantity (% w/w) |
|---|---|---|
| 1 | Isotretinoin | 8.47 |
| 2 | Meglumine | 1.06 |
| 3 | Water | q.s. |
| 4 | Hydroxypropyl methylcellulose | 4.26 |
| 5 | Lactose | 40.25 |
| 6 | Mannitol | 40.68 |
| 7 | Cremophor ® EL | 5.08 |
| 8 | Butylated hydroxyl toluene | 0.12 |
| 9 | Propyl gallate | 0.08 |

Procedure

1. Hydroxypropyl methylcellulose was dissolved in water.
2. Butylated hydroxyl toluene, propyl gallate, and meglumine were dissolved in the solution of step 1.
3. Isotretinoin was suspended in the solution of step 2.
4. The drug suspension of step 3 was milled in a Dyno®-mill containing zirconium beads to achieve a particle size of isotretinoin such that $D_{90}$ was about 2 μm.
5. Cremophor® EL was added at the end of the milling process.
6. The dispersion of step 5 was adsorbed onto a lactose and mannitol mixture in a fluid bed processor and dried.
7. The dried powder of step 6 was filled into size 00 capsules.

Dissolution Studies

I) The pharmaceutical composition of Example 8 (Test; 40 mg of isotretinoin) was compared with the marketed formulation of isotretinoin (Reference; 40 mg Epuris™ capsules) for the release profile in the FDA recommended dissolution medium as given below:

| Dissolution Media | 0.05M buffer pH 7.8 with 0.5% w/v N,N-dimethyl dodecylamine N-oxide |
|---|---|
| Apparatus/RPM/Vol | USP Type I (20 mesh basket)/100/900 mL |

| | % of Drug Released Over Time (minutes) | | | | | | |
|---|---|---|---|---|---|---|---|
| Sample | 15 | 30 | 45 | 60 | 90 | 120 | 180 |
| Test | 94 | 99 | 99 | 100 | 100 | 100 | 100 |
| Reference | 1 | 9 | 24 | 49 | 89 | 100 | 100 |

From the above data, it is evident that the test product has a better dissolution profile in comparison to the reference product.

II) The pharmaceutical composition of Example 8 (Test; 32 mg of isotretinoin) was compared with the marketed formulation of isotretinoin (Reference; 40 mg Absorica® capsules) for the release profile in the FDA recommended dissolution medium as given below:

| Dissolution Media | 0.05M buffer pH 7.8 with 0.5% w/v N,N-dimethyl dodecylamine N-oxide |
|---|---|
| Apparatus/RPM/Vol | USP Type I (20 mesh basket)/100/900 mL |

| | % of Drug Released Over Time (minutes) | | | | | |
|---|---|---|---|---|---|---|
| Sample | 15 | 30 | 45 | 60 | 90 | 120 |
| Test | 95 | 95 | 96 | 96 | 96 | 96 |
| Reference | 0 | 2 | 9 | 18 | 54 | 79 |

From the above data, it is evident that the test product has a better dissolution profile in comparison to the reference product at a lower dose, wherein the dose is at least 20% lower.

Pharmacokinetic Study Under Fed Condition

The pharmaceutical composition of Example 8 (Test; 40 mg of isotretinoin) was compared with the marketed formulation of isotretinoin (Reference; 40 mg Epuris™ capsules) under fed conditions on 18 healthy adult male subjects, out of these 15 subjects completed all three periods of the study.

Values for various pharmacokinetic parameters, including observed $C_{max}$, $AUC_{0-t}$, and $AUC_{0-inf}$ were calculated and are provided in Table 1 below.

TABLE 1

Comparative Pharmacokinetic Data for Test and Reference in 15 Healthy Adult Human Male Subjects:

| Parameter | In $C_{max}$ | In $AUC_{0-t}$ | In $AUC_{0-inf}$ |
|---|---|---|---|
| Ratio (T/R) | 125.41 | 116.55 | 116.48 |
| 90% CI | 112.76-139.47 | 111.51-121.83 | 111.72-121.46 |

Average $T_{max}$ values for the test and reference were 2.6778 hours and 6.1444 hours, respectively.

Under fed conditions, the Test prototype showed 1.25-fold higher $C_{max}$ and 1.16-fold higher AUC as compared to the reference. However, we do observe that for AUC, T/R ratio and 90% CI are within acceptable limits of 80% to 125%.

Pharmacokinetic Study Under Fasting Condition

The pharmaceutical composition of Example 8 (Test; 40 mg of isotretinoin) was compared with the marketed formulation of isotretinoin (Reference; 40 mg Epuris™ capsules) under fasting conditions on 18 healthy adult male subjects, out of these 14 subjects completed all three periods of the study.

Values for various pharmacokinetic parameters, including observed $C_{max}$, $AUC_{0-t}$, and $AUC_{0-inf}$ were calculated and are provided in Table 2 below.

TABLE 2

Comparative Pharmacokinetic Data for Test and Reference in 14 Healthy Adult Human Male Subjects:

| | In $C_{max}$ | In $AUC_{0-t}$ | In $AUC_{0-inf}$ |
|---|---|---|---|
| Ratio (T/R) | 340.10 | 250.36 | 243.25 |
| 90% CI | 275.29-420.15 | 217.9-287.66 | 213.22-277.5 |

Test prototype under fasting condition showed 3.4-fold higher $C_{max}$ and 2.5-fold higher AUC as compared to Reference.

The Effect of Food on the Test Formulation of Example 8 (40 mg Capsules) was also Evaluated and Results are Given in Table 3.

Reference (R): Epuris™ 40 mg capsules.
Test (T): Isotretinoin 40 mg capsules (Example 8).

TABLE 3

Relative effect of food (Calculated in number of fold (Fed/Fasting) on Isotretinoin capsule 40 mg)

| Formulation | $C_{max}$ | $AUC_{0-t}$ |
|---|---|---|
| Test | 0.71 | 0.99 |
| Reference | 1.95 | 2.12 |

The above data indicates that:
The extent of absorption for the Test prototype under fasting and fed conditions are comparable (0.99) to each other, whereas $C_{max}$ under fed conditions is lower than in fasting condition (approx. 0.7-fold).
For Epuris™, both AUC and $C_{max}$ under fed condition are ~2-fold higher than under fasted condition.

Study to Evaluate if a Dose Reduction of Example 8 Test Formulation can be Achieved, and Would that Formulation Still be Bioequivalent to Epuris™ Under Fasted and Fed Conditions.

Test (T): Isotretinoin 36 mg capsules (Example 8).
Reference (R): Epuris™ 40 mg capsules.
Simulated T/R ratios for Test under fasting and fed conditions versus Epuris™ under fed condition.

| | Simulated T/R ratios | |
|---|---|---|
| Parameter | Test - Fasting/ Reference - Fed | Test - Fed/ Reference - Fed |
| $C_{max}$ | 160.44 | 114.35 |
| $AUC_{0-t}$ | 105.84 | 104.82 |

The above evaluation indicates the following:
The Test prototype (dose corrected to 36 mg under fasting condition) is expected to provide approx. 1.6-fold higher $C_{max}$ as compared to Epuris™ fed whereas AUC is comparable to Epuris™ fed.

Conclusion
The Test prototype under fasting and fed conditions has a higher or enhanced bioavailability in comparison to the Reference product when dosed under fed condition.

Example 9

| S. No. | Ingredients | Quantity (% w/w) |
|---|---|---|
| 1 | Isotretinoin | 8.47 |
| 2 | Hydroxypropyl methylcellulose | 4.26 |
| 3 | Butylated hydroxyl toluene | 0.14 |
| 4 | Propyl gallate | 0.095 |
| 5 | Water | q.s. |
| 6 | Lactose | 41.27 |
| 7 | Mannitol | 40.69 |
| 8 | Kolliphor® EL | 5.08 |

Procedure
1. Hydroxypropyl methylcellulose was dissolved in water.
2. Butylated hydroxyl toluene and propyl gallate were dissolved in the solution of step 1.
3. Isotretinoin was suspended in the solution of step 2.
4. The drug suspension of step 3 was milled in a Dyno®-Mill containing zirconium beads to achieve a particle size of isotretinoin such that $D_{90}$ was about 2 μm.
5. Kolliphor® EL was added at the end of the milling process.
6. The dispersion of step 5 was adsorbed onto a lactose and mannitol mixture in a fluid bed processor and dried.
7. The dried powder of step 6 was filled into capsules.

We claim:

1. An oral pharmaceutical composition of isotretinoin and a carrier substrate having enhanced bioavailability over a capsule comprising a semi-solid suspension of isotretinoin, wherein the isotretinoin of said oral pharmaceutical composition having enhanced bioavailability is in the form of gel, dispersion, solution, suspension, or emulsion, adsorbed onto a carrier substrate selected from the group consisting of lactose, microcrystalline cellulose, calcium phosphate, dextrin, dextrose, sucrose, mannitol, maltodextrin and sodium alumino silicate to form solid particles, powder, or granules.

2. The oral composition according to claim 1, wherein said composition exhibits a mean $C_{max}$ and AUC under fed condition which is about 1.25 and about 1.16 times higher than the mean $C_{max}$ and AUC of a capsule comprising a semi-solid suspension of isotretinoin under fed condition, respectively.

3. The oral composition according to claim 1, wherein said composition exhibits a mean $C_{max}$ and AUC under fasting condition which is about 3.4 and about 2.5 times higher than the mean $C_{max}$ and AUC of a capsule comprising a semi-solid suspension of isotretinoin under fasting condition, respectively.

4. The oral composition according to claim 1, wherein said composition releases more than 50% of isotretinoin in 15 minutes in a media with a pH of 7.4 to 10.5.

5. The oral composition according to claim 1, wherein said enhancement in the bioavailability is directly correlated to a reduction in dose in order to have a bioequivalent product.

6. The oral composition according to claim 5, wherein the dose is reduced by at least 10% in comparison to a capsule comprising a semi-solid suspension of isotretinoin.

7. The oral composition according to claim 5, wherein the dose is reduced by at least 20% in comparison to a capsule comprising a semi-solid suspension of isotretinoin.

8. The oral composition according to claim 1, wherein said composition comprises isotretinoin and a pharmaceutically acceptable excipient.

9. The oral composition according to claim 1, wherein the carrier substrate is present in an amount of about 1% w/w to about 90% w/w by total weight of the composition.

10. The oral composition according to claim 9, wherein the carrier substrate is present in an amount of about 20% w/w to about 85% w/w by total weight of the composition.

11. The oral composition according to claim 1, wherein said composition further comprises a surfactant, a surface stabilizer, an antioxidant, or an alkaline stabilizer.

12. The oral composition according to claim 11, wherein said composition comprises isotretinoin, meglumine, a surface stabilizer, a surfactant, and a carrier substrate.

13. The oral composition according to claim 1, wherein said solid particles, powder, or granules are filled into capsules or processed with tablet adjuvants and compressed into tablets.

14. The oral composition according to claim 1, wherein said composition comprises isotretinoin in an amount of about 1 mg to 100 mg, 5 mg to 50 mg, 10 mg to 40 mg, 9 mg to 36 mg, or 8 mg to 32 mg.

15. The oral composition according to claim 14, wherein said composition comprises isotretinoin in an amount of about 40 mg, 32 mg, 28 mg, 24 mg, 20 mg, 16 mg, or 8 mg.

16. The oral composition according to claim 1, wherein the particle size distribution of isotretinoin is such that $D_{90}$ is less than 60 μm, less than 55 μm, less than 50 μm, less than 45 μm, less than 40 μm, less than 35 μm, less than 30 μm, less than 25 μm, less than 20 μm, less than 15 μm, or less than 10 μm.

17. The oral composition according to claim 1, wherein the particle size distribution of isotretinoin is such that $D_{50}$ is less than 40 μm, less than 35 μm, less than 30 μm, less than 25 μm, less than 20 μm, less than 15 μm, less than 10 μm, or less than 5 μm.

18. The oral composition according to claim 1, wherein the particle size distribution of isotretinoin is such that $D_{10}$ is less than 20 μm, less than 18 μm, less than 17 μm, less than 15 μm, less than 12 μm, less than 10 μm, less than 8 μm, less than 7 μm, less than 5 μm, or less than 2 μm.

19. The oral composition according to claim 8, wherein said composition is stable when stored at 40° C. and 75% relative humidity or at 25° C. and 60% relative humidity for a period of at least three months.

20. An oral pharmaceutical composition of isotretinoin having enhanced bioavailability over a capsule comprising a semi-solid suspension of isotretinoin, wherein the oral pharmaceutical composition is stable when stored at 40° C. and 75% relative humidity or at 25° C. and 60% relative humidity for a period of at least three months, wherein said composition is prepared using a process that comprises the following steps:
 (a) dissolving/dispersing an antioxidant in water, a water-miscible solvent, or a combination thereof;
 (b) adding one or more excipients selected from a surfactant, a surface-stabilizer, and an alkaline stabilizer to the solution or dispersion of step (a) to form a gel, a dispersion, a solution, a suspension, or an emulsion;
 (c) dissolving/dispersing isotretinoin into the gel, dispersion, solution, suspension, or emulsion of step (b);
 (d) optionally milling the gel, dispersion, solution, suspension, or emulsion of step (c);
 (e) adsorbing the gel, dispersion, solution, suspension, or emulsion of step (d) onto a carrier substrate selected from the group consisting of lactose, microcrystalline cellulose, calcium phosphate, dextrin, dextrose, sucrose, mannitol, maltodextrin and sodium alumino silicate to obtain solid particles, powder, or granules; and
 (f) filling the solid particles, powder, or granules of step (e) into capsules or processing the solid particles, powder, or granules of step (e) with tablet adjuvants and compressing into tablets.

21. A process for preparing an oral pharmaceutical composition of isotretinoin having enhanced bioavailability comprising:
 (a) isotretinoin;
 (b) meglumine;
 (c) a surfactant;
 (d) a surface stabilizer; and
 (e) a carrier substrate;
wherein the process comprises:
 i. dissolving/dispersing meglumine, a surfactant, and a surface stabilizer in water;
 ii. dispersing isotretinoin into the solution of step i;
 iii. milling the dispersion of step ii in a milling apparatus;
 iv. adsorbing the milled dispersion of step iii onto a carrier substrate to obtain solid particles, powder, or granules; and
 v. filling the solid particles, powder, or granules of step iv into capsules or processing the solid particles, powder, or granules of step iv with tablet adjuvants and compressing into tablets.

22. The process according to claim 21, wherein in step i, an antioxidant is added.

23. The process according to claim 21, wherein the pH of the dispersion obtained in step iii, or the solid particles, powder, or granules obtained in step iv, when dispersed in water, ranges from 3 to 11 or ranges from 7 to 10.

24. The oral pharmaceutical composition according to claim 1, wherein said composition is used for the treatment of acne, musculoskeletal and connective tissue inflammations, emphysema, ulcerating diseases, cervical tumors in HIV positive women, lung cancer in smokers, skin cancer, neuroblastoma, recurrent prostate cancer, leukemia, high-grade glioma, head and neck cancers, multiple myeloma, gram-negative folliculitis, recalcitrant rosacea, pyoderma faciale, psoriasis, cutaneous lupus erythematosus, acne fulminans, squamous cell carcinoma, and cutaneous photoaging.

* * * * *